(12) United States Patent
Chatterjee et al.

(10) Patent No.: US 10,154,814 B2
(45) Date of Patent: *Dec. 18, 2018

(54) WEARABLE PERSONAL INFORMATION SYSTEM

(71) Applicant: Microsoft Technology Licensing, LLC, Redmond, WA (US)

(72) Inventors: Monique Chatterjee, Seattle, WA (US); Carl Ledbetter, Mercer Island, WA (US); Sung Ho Son, Redmond, WA (US); Stephen Michael Christopher, Chicago, IL (US); Michael Jerome Ferlan, Black Diamond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,460

(22) Filed: Jul. 11, 2016

(65) Prior Publication Data

US 2016/0317087 A1 Nov. 3, 2016

Related U.S. Application Data

(63) Continuation of application No. 13/663,325, filed on Oct. 29, 2012, now Pat. No. 9,386,932.

(51) Int. Cl.
*A61B 5/00* (2006.01)
*A61B 5/024* (2006.01)
(Continued)

(52) U.S. Cl.
CPC .......... *A61B 5/681* (2013.01); *A61B 5/02438* (2013.01); *A61B 5/1112* (2013.01);
(Continued)

(58) Field of Classification Search
CPC .......... A61B 2562/0219; A61B 5/0205; A61B 5/0245; A61B 5/681; A61B 5/6802;
(Continued)

(56) References Cited

U.S. PATENT DOCUMENTS 4,769,799 A 9/1988 Matsukage
6,529,754 B2 3/2003 Kondo
(Continued)

FOREIGN PATENT DOCUMENTS

CN 101460100 A 6/2009
CN 101773387 A 7/2010
(Continued)

OTHER PUBLICATIONS

"Office Action Issued in European Patent Application No. 13786826.1", dated Feb. 8, 2017, 7 Pages.
(Continued)

*Primary Examiner* — Sanjay Cattungal
(74) *Attorney, Agent, or Firm* — Alleman Hall Creasman & Tuttle LLP

(57) ABSTRACT

A personal information system is provided. The system may include a portable information device having a housing including a top surface defined at least partially by a display, a bottom surface configured with a central region in which an optical sensor, electrical connector, and data connector are positioned, the housing enclosing an internal volume in which a processor is provided, the top surface and bottom surface being coupled by a perimeter side edge extending therebetween, and a mounting structure formed at least partially around the perimeter side edge of the housing. The system may further include a frame, which may be connected to a band, the frame surrounding a void and configured to receive the mounting structure, the frame and mounting structure being releasably securable via a tongue
(Continued)

and groove connection. The system may further comprise a dock to which the information device may be connected.

20 Claims, 5 Drawing Sheets

(51) Int. Cl.
*A61B 5/11* (2006.01)
*G06F 1/16* (2006.01)
*G04G 17/08* (2006.01)
*G04G 21/02* (2010.01)

(52) U.S. Cl.
CPC ........... *G04G 17/08* (2013.01); *G04G 21/025* (2013.01); *G06F 1/163* (2013.01); *G06F 1/1626* (2013.01); *G06F 1/1632* (2013.01); *A61B 2562/185* (2013.01); *Y10T 29/49826* (2015.01)

(58) Field of Classification Search
CPC ............ A61B 5/6824; A61B 2562/185; A61B 2230/65; A61B 5/02438; A61B 5/1112; A63B 71/0686; A63B 2230/65; G06F 1/1632; G06F 1/1626; G06F 1/163; G04G 21/025; G04G 17/08; Y10T 29/49826
See application file for complete search history.

(56) References Cited

U.S. PATENT DOCUMENTS

| | | | |
|---|---|---|---|
| 7,664,606 | B2 | 2/2010 | Suzuki et al. |
| 7,683,252 | B2 | 3/2010 | Oliver et al. |
| 7,805,186 | B2 | 9/2010 | Pulkkinen et al. |
| 8,157,732 | B2 | 4/2012 | Suzuki et al. |
| 8,289,162 | B2 | 10/2012 | Mooring et al. |
| 2002/0151775 | A1 | 10/2002 | Kondo |
| 2004/0057578 | A1 | 3/2004 | Brewer |
| 2006/0004265 | A1 | 1/2006 | Pulkkinen et al. |
| 2006/0245152 | A1 | 11/2006 | Chauhan |
| 2007/0113726 | A1 | 5/2007 | Oliver et al. |
| 2007/0118043 | A1 | 5/2007 | Oliver et al. |
| 2008/0004811 | A1 | 1/2008 | Suzuki et al. |
| 2008/0242956 | A1 | 10/2008 | Suzuki et al. |
| 2009/0069045 | A1 | 3/2009 | Cheng |
| 2010/0059649 | A1 | 3/2010 | Buxton |
| 2011/0157022 | A1 | 6/2011 | Goldburt |
| 2011/0176395 | A1 | 7/2011 | Mooring |
| 2011/0214030 | A1 | 9/2011 | Greenberg et al. |
| 2012/0081852 | A1 | 4/2012 | Maravilla et al. |
| 2012/0092822 | A1 | 4/2012 | Mooring et al. |
| 2013/0176142 | A1 | 7/2013 | Drysdale et al. |
| 2014/0122958 | A1 | 5/2014 | Greenberg et al. |

FOREIGN PATENT DOCUMENTS

| | | | |
|---|---|---|---|
| JP | S6073025 | U | 5/1985 |
| JP | S6180063 | U | 5/1986 |
| JP | S61189216 | U | 11/1986 |
| JP | S62233144 | A | 10/1987 |
| JP | S62192281 | U | 12/1987 |
| JP | S6363879 | U | 4/1988 |
| JP | H01167686 | U | 11/1989 |
| JP | 3010773 | U | 5/1995 |
| JP | 3065423 | U | 2/2000 |
| JP | 2000312670 | A | 11/2000 |
| JP | 2001188630 | A | 7/2001 |
| JP | 2001276001 | A | 10/2001 |
| JP | 2004028918 | A | 1/2004 |
| JP | 2004358258 | A | 12/2004 |
| JP | 2005055424 | A | 3/2005 |
| JP | 2005160641 | A | 6/2005 |
| JP | 2005270545 | A | 10/2005 |
| JP | 2005536260 | A | 12/2005 |
| JP | 2007085883 | A | 4/2007 |
| JP | 2008168054 | A | 7/2008 |
| JP | 2010264247 | A | 11/2010 |
| JP | 2010537674 | A | 12/2010 |
| JP | 2011509643 | A | 3/2011 |
| WO | 2004019172 | A2 | 3/2004 |

OTHER PUBLICATIONS

"Office Action and Search Report Issued in Chinese Patent Application No. 201380056874.2", dated Aug. 3, 2017, 15 Pages.

"Office Action Issued in Japanese Patent Application No. 2015-539768", dated Aug. 3, 2017, 19 Pages.

"ElectroTextiles Soft Technology Shown at New York Museum of Modern Art," ElectroTextiles Press Release, Retrieved Online at http://www.emailwire.com/release/printPR.php?content=showPR&prID=688, Published Feb. 12, 2001, 1 page.

Poh, M. et al., "A Wearable Sensor for Unobtrusive, Long-Term Assessment of Electrodermal Activity," IEEE Transactions on Biomedical Engineering, vol. 57, No. 5, May 2010, Current Version Published Apr. 21, 2010, 10 pages.

"TikTok+LunaTik Multi-Touch Watch Kits by Scott Wilson + Minimal," Kickstarter Website, Retrieved Online at www.kickstarter.com/profiles/1104350651/tiktok-lunatik-multi-touch-watch-kits, Retrieved Jul. 12, 2012, 4 pages.

ISA European Patent Office, International Search Report and Written Opinion Issued in Application No. PCT/US2013/066472, dated Jan. 8, 2014, WIPO, 12 pages.

United States Patent and Trademark Office, Office Action Issued in U.S. Appl. No. 13/663,325, dated Jul. 31, 2014, 9 pages.

United States Patent and Trademark Office, Office Action Issued in U.S. Appl. No. 13/663,325, dated Feb. 26, 2015, 10 pages.

United States Patent and Trademark Office, Office Action Issued in U.S. Appl. No. 13/663,325, dated Aug. 27, 2015, 10 pages.

United States Patent and Trademark Office, Notice of Allowance Issued in U.S. Appl. No. 13/663,325, dated Mar. 18, 2016, 7 pages.

"Summons to Attend Oral Proceedings Issued in European Patent No. 13786826.1", dated Jan. 22, 2018, 8 Pages.

"Second Office Action Issued in China Patent Application No. 201380056874.2", dated Apr. 17, 2018, 13 Pages.

"Notice of Allowance Issued in Japanese Patent Application No. 2015-539768", dated Mar. 1, 2018, 5 Pages.

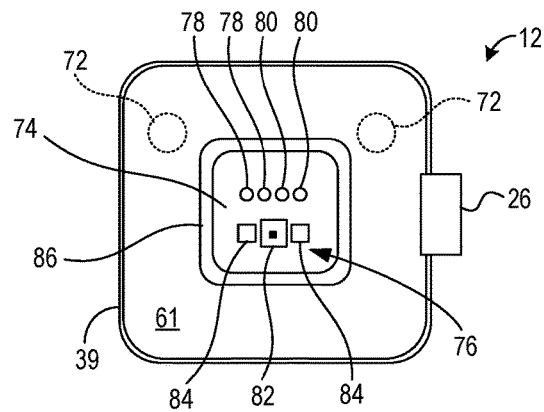
FIG. 5
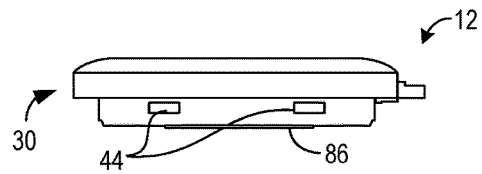
FIG. 9
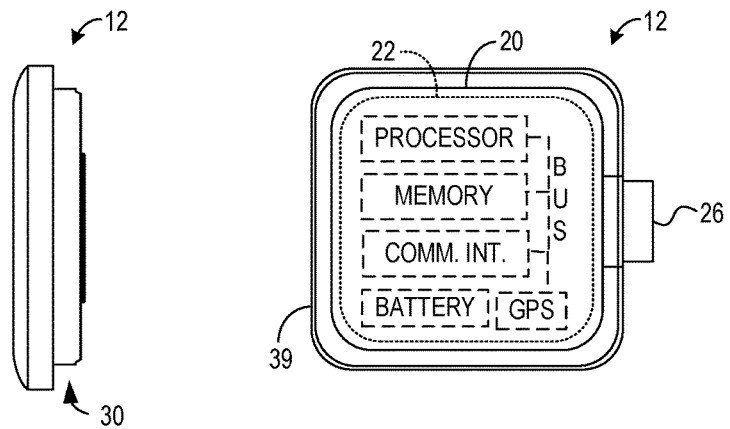
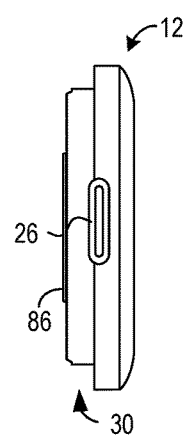
FIG. 10     FIG. 6     FIG. 8
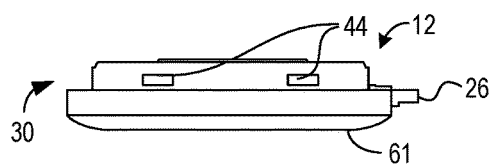
FIG. 7

WEARABLE PERSONAL INFORMATION SYSTEM

CROSS REFERENCE TO RELATED APPLICATIONS

This application is a continuation of U.S. patent application Ser. No. 13/663,325, filed on Oct. 29, 2012, and titled "WEARABLE PERSONAL INFORMATION SYSTEM", the entire disclosure of which is hereby incorporated herein by reference.

BACKGROUND

Portable electronic devices of increasingly small form factors have been developed recently which are tailored for use during exercise and outdoor activities. These devices may include GPS systems, altimeters, and stopwatches, for example, and may track a user's speed, position and time while running, bicycling, skiing, etc. One problem with such devices is that they are exposed to the user's perspiration, and can become soiled. Some prior devices have incorporated removable hook and loop fastener fabric wristbands that are washable; however, removing the fasteners for washing can be cumbersome and cause wear and tear on the band as it is repeatedly inserted and removed from securing ring, for example. Another problem with such devices is that they typically do not present the user with information during exercise other than time and position information. Users have been forced to connect external heartbeat sensors, for example using a chest strap, to obtain biometric feedback during exercise. The use of multiple components in this manner can be bulky and make exercise awkward. As a result, the adoption of such portable electronic devices during exercise is not as widespread as it could be.

SUMMARY

A personal information system is provided. The system may include a portable information device having a housing including a top surface defined at least partially by a display, a bottom surface in which an electrical connector and data connector are positioned, the housing enclosing an internal volume in which a processor is provided, the top surface and bottom surface being coupled by a perimeter side edge extending therebetween, and a mounting structure formed at least partially around the perimeter side edge of the housing. The system may further include a frame, which may be connected to a band, the frame surrounding a void and configured to receive the mounting structure, the frame and mounting structure being releasably securable via a tongue and groove connection. The system may further comprise a dock to which the information device may be connected.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 5 is a bottom side view of the information device of FIG. 1.

FIG. 6 is a top side view of the information device of FIG. 1.

FIG. 7 is a rear side view of the information device of FIG. 1.

FIG. 8 is a front side view of the information device of FIG. 1.

FIG. 9 is a right side view of the information device of FIG. 1.

FIG. 10 is a left side view of the information device of FIG. 1.

DETAILED DESCRIPTION

Figure 1:
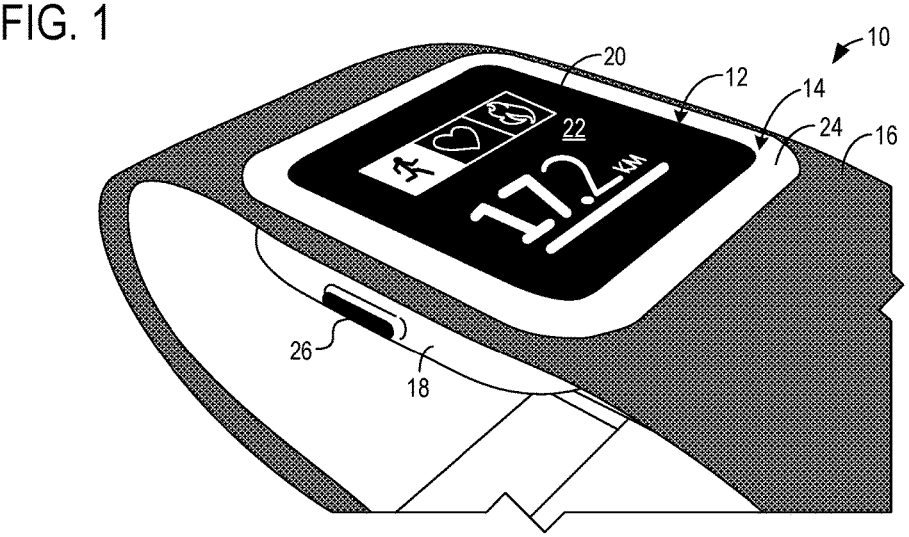
FIG. 1 is a partial perspective view of a personal information system including an information device coupled to a frame of a band, according to an embodiment of the present invention.
Figure 2:
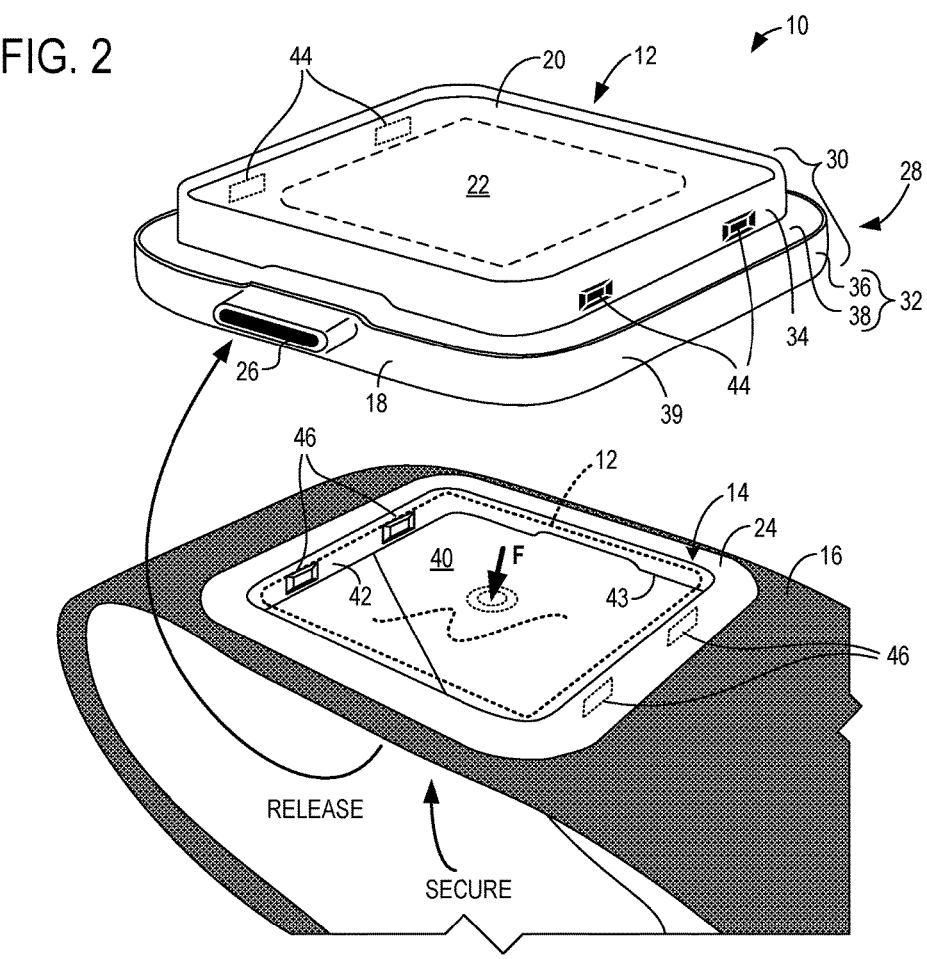
FIG. 2 is a partial exploded perspective view of the personal information system of FIG. 1, showing the information device removed from the frame of the band.

FIG. 1 illustrates a wearable personal information system 10. Personal information system 10 includes a portable information device 12 which is designed to be releasably secured in a frame 14 coupled to a wearable band 16, which in some embodiments may be elastic. As shown in FIG. 2, the information device 12 may be removed from the frame 14 by a force F of a user's hands for example, so that the band may be washed after exercise. The portable information device 12 may also be mounted in a dock, with or without the frame 14 and band 16 attached, for charging and data transmission with an external computing device, as explained below.

Continuing with reference to FIGS. 1 and 2, the information device 12 has a housing 18, which includes a top surface 20 at least partially defined by a display 22. In the depicted embodiment, the display 22 is configured to be flush with a top surface 24 of the surrounding frame 14 when releasably secured in the frame 14. In alternative embodiments, the display may extend proud of the top surface 24 of the frame 14, or be inset a distance below the top surface 24 of the frame 14. A button 26 may also be provided on the housing 18 to turn the device on and off, or to provide user control of other functions, such as a timer, stopwatch, etc.

To releasably secure the information device 12 to the frame 14 of the band 16, a mounting structure 28 is provided on the housing, which releasably detaches from the frame 14. The mounting structure 28 is formed at least partially (in the depicted embodiment, fully) around a perimeter side edge 30 of the housing 18. The mounting structure 28 includes a lip 32 formed at least partially around the perimeter side edge 30 of the frame 14. The lip 32 extends from a reduced perimeter wall 34 that is substantially vertical, and the lip 32 includes an enlarged perimeter wall 36 that is also substantially vertical, and a ledge 38, which is substantially horizontal, each of which extend at least partially (in the depicted embodiment, fully) around the perimeter side edge 30 of the housing 14. The enlarged perimeter wall 36 may be covered with a resiliently deformable seal member 39, typically made of an elastomeric material such as a flexible plastic or rubber, which helps secure the information device to the dock 50, as discussed below. It will be appreciated that the perimeter side edge 30 of the information device 12 has a shape that corresponds to the shape of an inside perimeter wall 42 of the frame 14. Other shapes are possible for the lip 32 of the mounting structure; for example, the ledge 36 may be angled downward or upward relative to horizontal, and the enlarged perimeter wall 38 may be angled inward and sloping toward the void 40 instead of vertical.

To releasably secure the information device 12 in the frame 14 of the band 16, the information device 12 is inserted from a bottom side of a void 40 surrounded by the frame 14. The inside perimeter wall 42 of the frame is configured with a shape that corresponds to the shape of the perimeter side edge 30, and the frame 14 is thus configured to snugly receive the information device 12. To accomplish this, reduced perimeter wall 34 is sized to slide within the inside perimeter wall 42, until ledge 38 contacts a bottom surface 43 of the frame 14 and a tongue and groove connection engages between the frame 14 and mounting structure 28. Contact of the bottom surface 43 of the inside perimeter wall 42 of the frame 14 and the ledge 38 of lip 32 stops ingress of the information device 12 into the frame 14 at a predetermined point, typically so that the top surface 20 of the frame is flush with the top surface 24 of the frame 14.

In the depicted embodiment the tongue and groove connection is formed by engagement of protrusions 44 formed on the reduced perimeter wall 34 of the mounting structure 28 and concavities 46 are formed on the inside perimeter wall 42 of the frame 14. In other embodiments other configurations are possible, such as protrusions 44 being formed on the frame and concavities 46 being formed on the information device, or a mixture thereof. In the depicted embodiment, a pair of protrusions 44 is formed on each of two opposite sides of the substantially square housing 18, and a pair of concavities is formed on each of two opposite sides of the inside perimeter wall 42 of the frame. In other embodiments, the size, number, and position of the protrusions 44 and concavities 46 may vary. For example, only one protrusion cavity pair may be formed on each of the opposite sides of the frame 14 and housing 18, or a protrusion/concavity may be formed on each of the four sides of the housing 18/frame 14.

Figure 3:
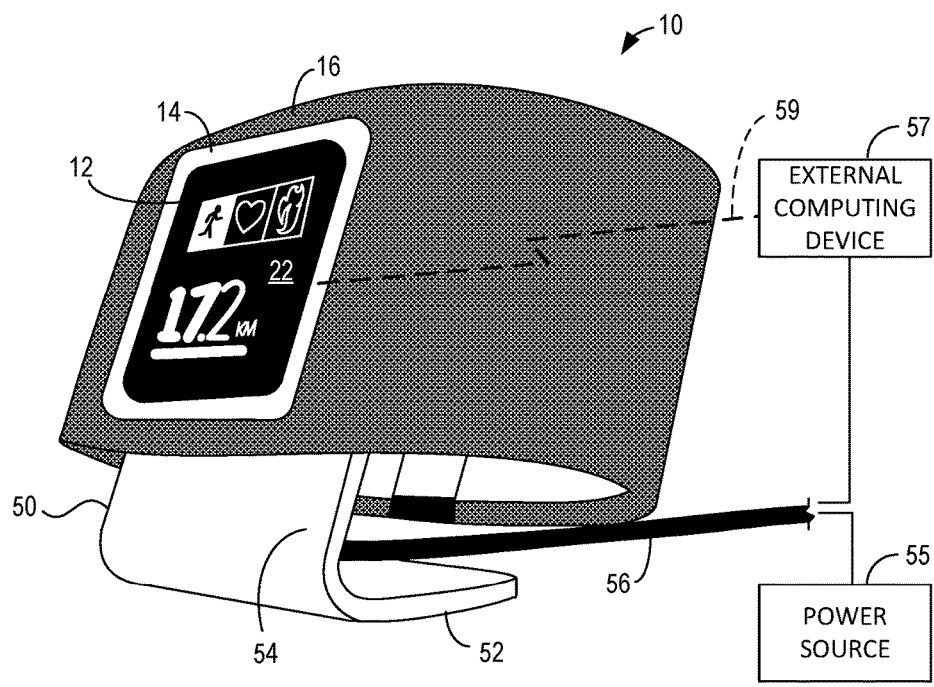
FIG. 3 is a perspective view showing the information device of the personal information system of FIG. 1, coupled to a first embodiment of a dock while the frame and band remain coupled to the information device.

As illustrated in FIG. 3, the personal information system 10 further includes a first embodiment of a dock 50 configured to receive and releasably secure the information device 12. The information device 12 may be secured in the dock 50 with the frame 14 and band 16 coupled thereto, or after being released and separated from the frame 14 and band 16. In the depicted embodiment, the dock 50 includes a base portion 52 and an upright portion 54. The base portion 52 includes a substantially horizontal bottom surface configured to rest on a level surface such as a table, and the upright portion 54 is angled slightly past vertical, to angle the display 22 of the information device 12 upward to provide a user a convenient view of the display. The base portion 52 and upright portion 54 may be manufactured of a single piece of material, which may be metal or plastic, by forming a bend therebetween, as shown.

A cord 56 extends from the dock 50. The cord 56 may be removable and/or interchangeable, and may be a power cord, a USB cord for transmitting power and data, etc. Accordingly, the cord may establish an electrical connection for charging with a power source 55, and the same cord or a different cord may establish a data connection with external computing device 57. In other embodiments, a wireless data connection 59 may be established directly between the information device 12 and the external computing device 57, or between the dock 50 and the external computing device 57, and a corded data connection may be omitted.

Figure 4:
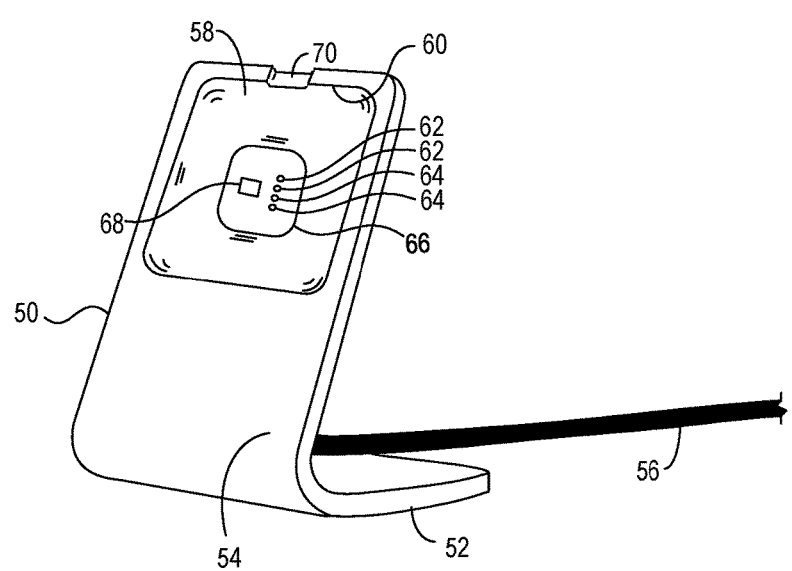
FIG. 4 is a perspective view showing the dock of FIG. 3, with the information device removed therefrom.

As shown in FIG. 4, the dock 50 may be configured with a mounting well 58 configured to receive and releasably secure the information device 12. The mounting well 58 has an outer perimeter wall 60 that is sized to accommodate the mounting structure 28 of the information device 12. The mounting well 58 has a curvature that is the mirror image of the curvature of the bottom surface 61 of the information device 12, shown in FIG. 7, for example. The resiliently deformable seal member 39 formed on the enlarged perimeter wall 38 snugly fits within the outer perimeter wall 60 of the mounting well by slightly deforming the seal member 37, to promote secure purchase of the information device by the mounting well 58. While the fit is tight enough to prevent the information device from accidentally falling out of the mounting well, the retaining force can easily be overcome by a user grasping the information device 12 and pulling it out of the mounting well 58 for use.

Returning to FIG. 4, the dock 58 further includes a pair of dock-side electrical connectors 62 and a pair of dock-side data connectors 64 in a central region 66 of the mounting well 58 of the dock 50. Although a pair of each such connectors are illustrated, it will be appreciated that one of each, or more than two of each, of each type of connector may be provided as alternatives. The central region 66 may be, for example, a central region in the shape of a rounded square, rectangle, circle or other curved or polygonal shape which is between one third and one half as wide and between one third and one half as tall as the width and height of the mounting well 58 itself. Further, while the dock-side electrical connectors 62 and dock-side data connectors 64 are shown grouped in the central region 66, it will be appreciated that in other embodiments they may not be grouped together but rather separated by a distance, and/or may be positioned in other locations outside the central region 66. Further, it will be appreciated that the central region 66 may be formed in sizes and shapes other than as illustrated. An indentation 68 may be provided to accommodate optical sensor 76, which stands proud of the bottom surface of the information device 12.

A notch 70 may be provided in a perimeter wall 60 of the mounting well 58, to accommodate the button 26 of the information device. The mounting well 58 may be manufactured all or partially of metal, or plastic over metal, and thus may be configured to releasably secure the information device 12 through the use of magnetic force. For this purpose, in the depicted embodiment as shown in FIG. 5, magnets 72 are provided adjacent a bottom surface 61 of the information device. Alternatively, the magnets 72 may be provided in the dock 50, or in both components.

FIG. 5 illustrates the detailed construction of the bottom surface 61 of the housing 18 of the information device 12. The bottom surface 61 is configured with a central region 74 in which an optical sensor 76, one or more electrical connectors 78, and one or more data connectors 80 may be positioned. While the optical sensor 76, electrical connectors 78, and data connectors 80 are shown grouped in the central region 74, it will be appreciated that in other embodiments they may not be grouped together but rather separated by a distance, and/or may be positioned in other locations outside the central region 74. Further, it will be appreciated that the central region 74 may be formed in sizes and shapes other than as illustrated. The optical sensor 76 includes a light emitter 82 and one or more light sensors 84. When the information device 12 is worn by the user, the light emitter 82 is configured to emit a light into the skin of a user, and the light sensor 84 is configured to sense reflected light from the emitter to measure a biometric parameter of a user. In some embodiments, the optical sensor 76 may be omitted.

The information device 12 may further include a light sealing gasket 86 formed on the bottom surface 61 of the information device 12 around the central region 74 so as to surround the optical sensor 76. When the information device 12 is worn by a user, the light sealing gasket 86 is configured to contact a surface of the skin of the user to substantially seal out external light, thereby enabling the optical sensor 76 to operate substantially without interference from external light. The light sealing gasket 86 is typically made of a resiliently deformable elastomeric material, such as rubber. In the depicted embodiment, the light sealing gasket 86 is formed to extend proud of the bottom surface 61. Alternatively, the light sealing gasket may be substantially flush with the bottom surface, and the central region 74 may be slightly inset relative to the bottom surface 61.

When the information device 12 is attached to the dock 50 described above, the electrical connectors 78 and data connectors 80 of the information device 12 are configured to connect to corresponding one or more dock-side electrical connectors 62 and one or more dock-side data connectors 64, to thereby charge the portable information device using power source 55 and transmit data to the external computing device 57. As discussed above, in some embodiments, only electrical connectors may be provided, and a data connection may be achieved wirelessly.

FIG. 6 illustrates a top surface 20 of the information device 12, while FIGS. 7, 8, 9, and 10 respectively illustrate left, front, right, and back sides of the perimeter side surface 30 of the information device 12. The top surface 20, bottom surface 61 and perimeter side surface 30 of the housing 14 collectively enclose an internal volume in which a processor and associated memory, communications interface, data bus, and GPS unit with internal compass are provided, as illustrated in FIG. 6. The communications interface is configured to transmit and receive data via the one or more data connectors 80, to thereby communicate with external computing devices. The processor communicates with the memory and the communications interface via a communications bus, and is configured to execute programs stored in memory, using portions of memory. A battery that is rechargeable via the one or more electrical connectors 78 is also provided within the housing. A program receives input from the optical sensor 76, data connectors 80, button 26, touch display 22, and other sources such as the GPS unit with internal compass, processes the input according to programmatic rules, and displays appropriate output on display 22. Specific examples of programs stored in memory on the information device 12 are given below.

As illustrated in FIG. 1, one program that may be executed by the processor of the information device 12 is configured to display a graphical user interface on the display 22. As discussed above, display 18 may be a touch-sensitive screen so as to receive touch input from the user. Thus, the display 18 may be configured to receive touch input from the user to select different functions of the program, to thereby display different data, etc. The program executed on the processor is configured to receive a signal from the optical sensors indicating a measured biometric parameter, and to display on the display an indication of the measured biometric parameter. In the depicted embodiment, selecting a running icon causes the program to display a current run length (17.2 km), which is tracked by the GPS unit in the information device 12. Pressing the heart icon causes the program to display a current pulse of the user. Pressing the fire icon causes the program to display an estimation of the calories consumed by the user during the current workout session. It will be appreciated that programs having other functionality may also be provided. For example, a music listening program, an alarm clock program, a messaging program, and a telephone program may additionally be provided.

Figure 11:
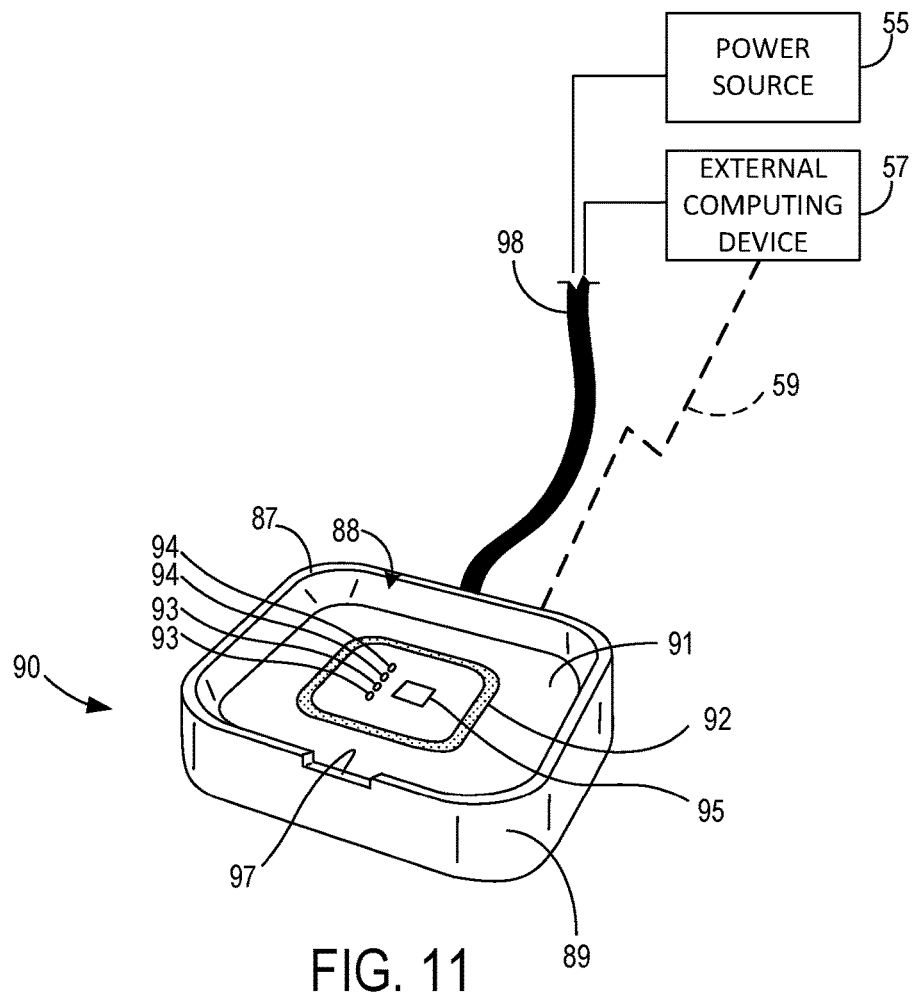
FIG. 11 is perspective view of a second embodiment of a dock, with the information device removed therefrom.
Figure 12:
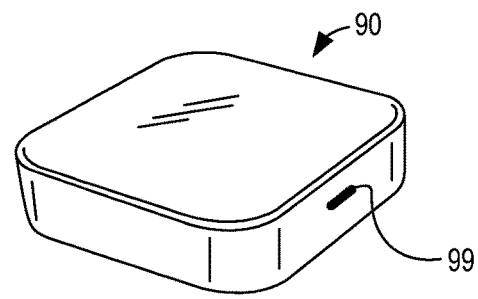
FIG. 12 is a bottom view of the dock of FIG. 11.

FIGS. 11 and 12 illustrate a second embodiment of a dock 90 configured to receive and releasably secure the information device 12. FIG. 11 shows the dock 90 having a perimeter wall 87 including an inside perimeter wall 88 and an outer perimeter wall 89. The dock is shown in FIG. 11 laying flat, however it will be appreciated that the dock can be placed upright on a side edge of the outer perimeter wall 89. In this orientation, the dock 90 can receive the information device 12 when coupled to a frame and band, or when released and separated from these elements.

FIG. 11 shows the dock 90 having a mounting well 91 being partially comprised of an inside perimeter wall 88 configured to receive and releasably secure the information device 12. The mounting well 91 is formed to match a size and curvature of the bottom surface 61 (FIG. 7) of the information device 12. A notch 97 may be included in the perimeter wall 87 to allow space for a button 26 of the information device 12 when secured in the dock. The mounting well 91 contains a central region 92 which is formed to accommodate a central region 74 on the bottom surface 61 of the information device 12, an example of which is shown in FIG. 5. The central region 92 within the mounting well 91 of the dock 90 contains dock-side electrical connectors 93 and a pair of dock-side data connectors 94. An indentation 95 may be included to surround and protect an optical sensor 76 (FIG. 5) which stands proud of the bottom surface 61 of the information device 12. It will be appreciated that the electrical connectors 93 and data connectors 94 may be present in suitable number and placement which corresponds and connects with electrical connectors 78 and data connectors 80 on the bottom surface 61 of the information device 12.

As described previously in reference to the first dock embodiment of FIGS. 3 and 4, the information device 12 may be releasably secured in the dock 90 by magnetic force, or a snap and lock mechanism, etc. Magnets 72 are shown in FIG. 5 as being contained within the information device 12, but may be provided in the dock 90, or in both components. The dock 90 may also be partially constructed of metal to enable a magnetic attachment between the dock 90 and information device 12. Dock 90 may be constructed of a smooth and continuous material such as a plastic or rubber, or another material or combination thereof. In some embodiments, the material of dock 90 may be elastomeric or resilient so that when information device 12 is inserted in the mounting well 91, the enlarged perimeter wall 36 of the information device 12 may interface with the material of the inside perimeter wall 88 of the mounting well 91 and further secure the device. Such an interface may be configured function as a snap and lock mechanism, which enables a user to "snap" the information device into a locked position in the mounting well. The retaining force of the magnetic and/or interfacing structures releasably secure the information device 12 within the dock 90. However, the retaining force can easily be overcome by a user grasping the information device 12 and pulling it out of the mounting well 61.

As shown in FIG. 11, a cord 98 extends from the dock 90. FIG. 12 provides an example wherein cord 98 is removable from the dock 90 to reveal a connector 99 located in the outer perimeter wall 89 of the dock. The connector 99 may be a micro-USB connector, USB connector or other connector. The cord 98 and connector 99 may establish an electrical connection for charging with a power source 55, and the same connector and cord or a different cord may establish a data connection with external computing device 57. As shown in FIG. 3, a wireless data connection 59 may be established directly between the information device 12 and the external computing device 57. The dock 90 may also be configured to have a wireless data connection 59 with the external computing device 57.

Figure 13:
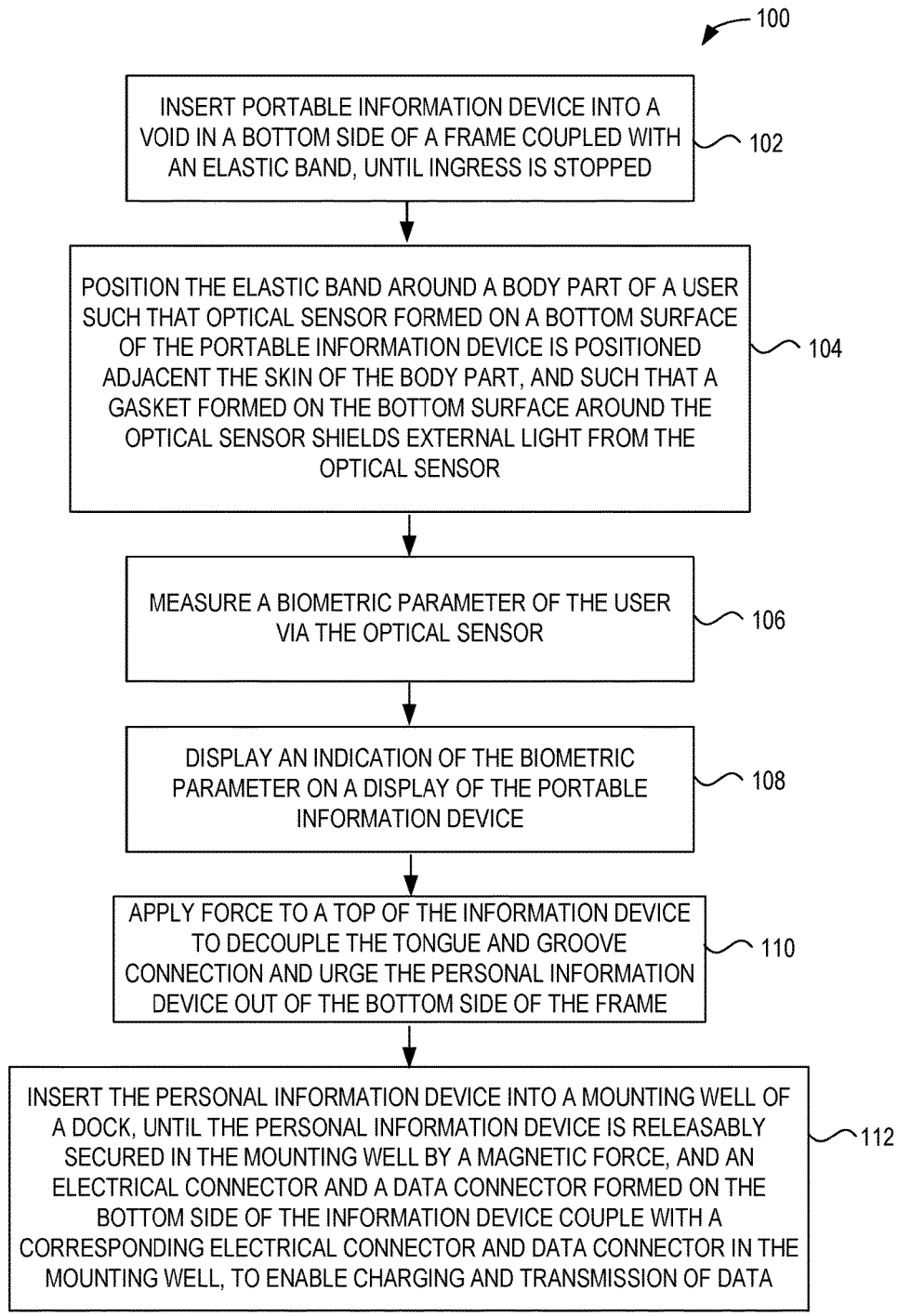
FIG. 13 is a flow diagram of a method of using a personal information system, according to one embodiment.

FIG. 13 illustrates a method 100 for use with a personal information system. The method may be practiced using a personal information system such as described above, or other suitable hardware system. At 102, the method includes inserting a portable information device into a void in a bottom side of a frame coupled with a band until ingress of the portable information device into the frame is stopped by contact between a lip formed in a mounting structure of the portable information device and a bottom surface of an inside perimeter wall of the frame, and a tongue and groove connection is established between the mounting structure and the frame, to thereby releasably secure the portable information device to the frame coupled to the band.

At 104, the method further includes positioning the band around a body part of a user such that an optical sensor formed on a bottom surface of a portable information device is positioned adjacent to the skin of the body part, and such that a gasket formed on the bottom surface around the optical sensor shields external light from the optical sensor. At 106, the method further includes measuring a biometric parameter of the user via the optical sensor. At 108, the method further includes displaying an indication of the biometric parameter, such as heart rate, on a display of the portable information device.

At 110, the method further includes applying a force to a top surface of a housing of the portable information device to decouple the tongue and groove connection and urge the portable information device out of the bottom side of the frame. At 112, the method further includes inserting the portable information device into a mounting well of a dock, until the portable information device is releasably secured in the mounting well, and an electrical connector and a data connector formed on the bottom side of the portable information device couple with a corresponding electrical connector and data connector in the mounting well, to enable charging and transmission of data. The portable information device may be secured in the mounting well by a magnetic force, or by another securing force such as a snap and lock mechanism, etc. The portable information device may be inserted into the mounting well while the portable information device is secured to the frame of the band, or while the portable information device is released and separated from the frame of the band.

The above described systems and methods provide a convenient approach to a wearable personal information system, which includes a portable information device with a mounting structure that can both attach to a frame and band, and attach to an associated dock. This enables the user to conveniently remove the frame and band from the information device after exercise to wash the frame and band, and to store the information device, band attached or not, in a dock which can facilitate charging and possibly data transfer while the information device is not in use.

It will be understood that numerous variations are possible to the above described embodiments. For example, frame 14 could be provided not attached to an band, but attached to another component such as a portable stand coupled to an exercise device. Further, a plurality of such frames and associated components could be provided, enabling the user to use one information device in a plurality of contexts. For example, the user could store the information device in the dock when not in use, run outside with the information device attached to the frame and band, or run on a treadmill on which the information device sits coupled to another frame which is part of a portable stand. Such portable stands could be provided on a variety of equipment, including bicycles, stair climbers, elliptical trainers, etc.

It will be appreciated that as used herein, the term "processor" describes a logic circuit, which may be an application specific integrated circuit (ASIC), complex programmable logic device (CPLD), system-on-chip (SOC), central processing unit (CPU) or other type of processor. The memory may include both persistent memory, such as FLASH memory or electrically erasable programmable memory (EEPROM), and volatile memory, such as RAM. Removable computer readable media such as an SD card may be provided to transfer data in some embodiments.

It will also be appreciated that as used herein, term "program" describes instructions stored in memory and executed by the processor to perform a particular function. The term "program" may encompass individual or groups of executable files, data files, libraries, drivers, scripts, database records, etc.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A personal information system, comprising:
   a portable information device having:
      a housing including a top surface defined at least partially by a display, a bottom surface in which an electrical connector is positioned, the housing enclosing an internal volume in which a processor is provided, the top surface and bottom surface being coupled by a perimeter side edge extending therebetween; and
      a mounting structure formed on a surface of the housing;
   a band having a void formed therein, a portion of the band surrounding the void having a complementary shape configured to surround the perimeter side edge of the housing and being configured to releasably secure to the mounting structure, the portion of the band and mounting structure being releasably securable via engagement and disengagement of a tongue and groove connection based on at least a force applied such that when the band is secured to the mounting structure the housing and the mounting structure are coupled to the band in an orientation in which the housing and the mounting structure extend into the void and the display of the portable information device is positioned so as to face upward from the void, wherein ingress of the housing and mounting structure into the void are stopped by contact of a laterally extending surface of the housing with a surface of the portion of the band.

2. The system of claim 1, further comprising a dock configured with a mounting well configured to receive and releasably secure the portable information device, the mounting well having an outer perimeter wall sized to accommodate the mounting structure of the portable information device.

3. The system of claim 2, wherein the bottom surface is configured with a central region within which the electrical connector is positioned, and wherein the dock further includes a corresponding dock-side electrical connector in a central region of the mounting well of the dock.

4. The system of claim 2, wherein the portable information device is releasably secured by magnets to the dock.

5. The system of claim 1,
wherein the portion of the band is a frame, and
wherein the laterally extending surface is a lip formed at least partially around a perimeter of the frame, a reduced perimeter wall of the mounting structure extending upwardly from the lip to the top surface and extending at least partially around the perimeter of the frame, the reduced perimeter wall having a shape that corresponds to the shape of an inside perimeter wall of the frame and the lip contacting a bottom surface of the frame when the mounting structure is engaged with the frame to stop ingress thereof.

6. The system of claim 5, wherein the housing is configured to be mounted to a mounting well of a dock while the frame is coupled to the housing.

7. The system of claim 1, wherein the bottom surface further includes an optical sensor, the optical sensor including a light emitter and at least one light sensor, and wherein the light emitter is configured to emit a light into the skin of a user, and the at least one light sensor is configured to measure a biometric parameter of the user, when the device is worn by the user.

8. The system of claim 7, further comprising a light sealing gasket formed on the bottom surface of the portable information device around a central region and surrounding the optical sensor, the light sealing gasket being configured to contact a surface of the user to seal out external light, thereby enabling the optical sensor to operate without interference from external light.

9. The system of claim 8, further comprising a program executed on the processor, which is configured to receive a signal from the optical sensor indicating a measured biometric parameter, and to display on the display an indication of the measured biometric parameter.

10. The system of claim 1, wherein a protrusion is formed on the perimeter side edge of the housing.

11. A personal information system, comprising:
an information device having:
a housing including a top surface defined at least partially by a display, a bottom surface configured with a central region in which an optical sensor and electrical connector are positioned, the housing enclosing an internal volume in which a processor is provided, the top surface and bottom surface being coupled by a perimeter side edge extending therebetween, the optical sensor being configured to measure a biometric parameter of a user of the device when the device is worn by the user, and the electrical connector being configured to connect to a corresponding connector on a dock to charge the information device; and
a mounting structure formed on a surface of the housing;
a band with a portion surrounding a void and having a complementary shape configured to surround the perimeter side edge of the housing, the portion of the band being configured to releasably secure to the mounting structure, the portion of the band and mounting structure being releasably securable via a tongue and groove connection based on at least a force applied such that when the portion of the band is secured to the mounting structure, the housing and the mounting structure are coupled to the portion of the band in an orientation in which the housing and the mounting structure extend into the void and the display of the information device is positioned facing upward from the void, wherein ingress of the housing and mounting structure into the void are stopped by contact of a laterally extending surface of the housing with a surface of the portion of the band;
wherein the mounting structure includes a lip as the laterally extending surface formed at least partially around a perimeter of the portion of the band surrounding the void, a reduced perimeter wall of the mounting structure extending upwardly from the lip to the top surface and extending at least partially around the perimeter of the portion of the band, the reduced perimeter wall having a shape that corresponds to a shape of an inside perimeter wall of the portion of the band and the lip contacting a bottom surface of the portion of the band when the mounting structure is engaged with the portion of the band to stop ingress thereof.

12. A method for use with a wearable personal information system, comprising:
inserting a portable information device having a housing and a mounting structure into a void in a portion of a band, the portion of the band having a complementary shape configured to surround a perimeter side edge of the housing of the portable information device, until ingress of the housing and mounting structure into the void are stopped by contact of a surface of the housing with a surface of the portion of the band, and a tongue and groove connection is established between the mounting structure and the portion of the band, such that when the portion of the band is secured to the mounting structure by engagement and disengagement of the tongue and groove connection, the portable information device is coupled to the band in an orientation in which the portable information device extends into the void and a display of the portable information device is positioned relative to the band so as to face upward from the void, to thereby releasably secure the portable information device to the band.

13. The method of claim 12, further comprising:
positioning the band around a body part of a user such that an optical sensor formed on a bottom surface of the housing of the portable information device is positioned adjacent the skin of the body part, and such that a gasket formed on the bottom surface of the housing around the optical sensor shields external light from the optical sensor.

14. The method of claim 13, further comprising:
measuring a biometric parameter of the user via the optical sensor; and displaying an indication of the biometric parameter on the display of the portable information device.

15. The method of claim 12, further comprising:
applying force to a top of the housing of the portable information device to decouple the tongue and groove connection and urge the portable information device out of the band.

16. The method of claim 15, further comprising:
inserting the portable information device into a mounting well of a dock, until the portable information device is releasably secured in the mounting well by a magnetic force and/or by a deformable seal member of the portable information device, and an electrical connector formed on the bottom surface of the housing of the portable information device couples with a corresponding electrical connector in the mounting well, to enable charging.

17. The method of claim 16, wherein inserting the portable information device into the mounting well is performed while the portable information device is coupled to the band.

18. The method of claim 16, wherein inserting the portable information device into the mounting well is performed while the portable information device is released and separated from the band.

19. The system of claim 11, wherein the portion of the band comprises a frame coupled to the band.

20. The personal information system of claim 11, further comprising:
the dock provided with a mounting well configured to receive and releasably secure the information device, the mounting well having an outer perimeter wall sized to accommodate the mounting structure of the information device, wherein the dock further includes a corresponding dock-side electrical connector in a central region of the mounting well of the dock, the corresponding dock-side electrical connector being configured to connect to the electrical connector of the information device when the information device is releasably secured in the mounting well.

* * * * *